United States Patent
Humphreys et al.

(10) Patent No.: US 8,374,461 B2
(45) Date of Patent: Feb. 12, 2013

(54) DIGITAL RADIOGRAPHY PLATE IDENTIFICATION SYSTEM

(75) Inventors: Geoffrey Humphreys, Baton Rouge, LA (US); Chad Lacour, Baton Rouge, LA (US)

(73) Assignee: Smartplates, LLC, Baton Rouge, LA (US)

( * ) Notice: Subject to any disclaimer, the term of this patent is extended or adjusted under 35 U.S.C. 154(b) by 29 days.

(21) Appl. No.: 13/180,886

(22) Filed: Jul. 12, 2011

(65) Prior Publication Data

US 2012/0039520 A1  Feb. 16, 2012

Related U.S. Application Data

(60) Provisional application No. 61/363,538, filed on Jul. 12, 2010.

(51) Int. Cl.
*G06K 9/32* (2006.01)
(52) U.S. Cl. ........ 382/291; 382/128; 382/295; 382/296; 128/922
(58) Field of Classification Search ............ 382/128, 382/130, 131, 132, 291, 295, 296; 128/920, 128/922
See application file for complete search history.

(56) References Cited

U.S. PATENT DOCUMENTS

| | | |
|---|---|---|
| 456,396 A | 7/1891 | Blakemore |
| 1,358,990 A | 11/1920 | Scannell |
| 1,396,415 A | 11/1921 | Fried |
| 1,632,154 A | 6/1927 | Torpin |
| 1,917,433 A | 7/1933 | Cressler |
| 3,619,611 A | 11/1971 | Hall |
| 3,703,272 A | 11/1972 | Lareau |
| 3,942,016 A | 3/1976 | Schatz |
| 3,962,807 A | 6/1976 | Pantone |
| 4,127,774 A | 11/1978 | Gillen |
| 4,194,122 A | 3/1980 | Mitchell et al. |
| 4,204,639 A | 5/1980 | Barber et al. |
| 5,179,579 A | 1/1993 | Dove et al. |
| 5,195,123 A | 3/1993 | Clement |
| 6,041,102 A | 3/2000 | Francsis |
| 6,354,737 B1 | 3/2002 | Hufe et al. |
| 6,679,847 B1 * | 1/2004 | Robinson et al. ............ 600/447 |
| 7,358,502 B1 * | 4/2008 | Appleby et al. ......... 250/370.14 |
| 7,627,370 B2 * | 12/2009 | Marks ............................ 600/544 |
| 7,787,687 B2 * | 8/2010 | Miyano et al. ................ 382/149 |
| 7,987,003 B2 * | 7/2011 | Hoffberg et al. ................ 700/17 |
| 2006/0098785 A1 | 5/2006 | Woods |
| 2008/0084965 A1 | 4/2008 | Ohnona et al. |

FOREIGN PATENT DOCUMENTS

EP  1 649 812 A1  4/2006

OTHER PUBLICATIONS

Gendex Dental Systems, "Additional Mount Information", Imaging Software: VixWin Platinum User Manual, 2009, pp. 8-4-8-9.
Gendex Dental Systems, "Accelerated Workflow", VixWin Platinum Brochure, 2000, pp. 5.

* cited by examiner

*Primary Examiner* — Yosef Kassa
(74) *Attorney, Agent, or Firm* — Saliwanchik, Lloyd & Eisenschenk (57) ABSTRACT

Systems, devices, and methods for facilitating the automatic identification, sorting, and positioning of radiographic images. According to one embodiment of the subject invention, phosphorous plates for intra-oral imaging are encoded for automated image set identification, location, and orientation. In certain embodiments, a processing system is able to process encoded identifiers on the phosphorous plates with digitized images depicted on the phosphorous plates to automatically identify, sort, and rotate the digitized images into proper orientations for user viewing.

31 Claims, 6 Drawing Sheets

PSP ID System Utilizing Unique PSPs in ALL Template Positions
(50 unique plates)

Master PSPs (dictate the template and carry the image for position 1)

| Set/Plate ID | Set Position | Plate Ct. | Set Desc. | Rotation | Flip | Mirror | Color | Visual ID |
|---|---|---|---|---|---|---|---|---|
| A | 1 | 20 | Adult FMX | 0 | No | No | Red | AFMX |
| B | 1 | 8 | PEDO FMX | 0 | No | No | Purple | PFMX |
| C | 1 | 4 | 4 Horiz. BWX | 0 | No | No | Green | H4BW |
| D | 1 | 4 | 4 Vert. BWX | 90° CW | No | No | Blue | V4BW |
| E | 1 | 4 | PEDO BWX + PAX | 0 | No | No | Yellow | PBWX |
| F | 1 | 7 | 7 Vert. BWX | 90° CW | No | No | Orange | V7BW |
| G | 1 | 1 | SingleShot-H | 0 | No | No | Lt.Blue | H-SS |
| H | 1 | 1 | SingleShot-V | 90° CW | No | No | Gold | V-SS |
| I | 1 | 1 | Sgl-Shot-V-CCW | 90° CCW | No | No | White | VCCW |

FIG. 1

Subordinate PSPs (positions are fixed within individual Sets/Templates)

| Set/Plate ID | Template = | Position = | Set Desc. | Rotation = | Flip | Mirror | Color | Visual ID |
|---|---|---|---|---|---|---|---|---|
| A-2 | A | 2 | Adult FMX | 0 | No | No | Red | AFMX-2 |
| B-2 | B | 2 | PEDO FMX | 0 | No | No | Purple | PFMX-2 |
| C-2 | C | 2 | 4 Horiz. BWX | 0 | No | No | Green | HBWX-2 |
| D-2 | D | 2 | 4 Vert. BWX | 90° CW | No | No | Blue | VBWX-2 |
| E-2 | E | 2 | PEDO BWX + PAX | 0 | No | No | Yellow | PBWPA-2 |
| F-2 | F | 2 | 7 Vert. BWX | 90° CW | No | No | Orange | 7BWX-2 |
| A-3 | A | 3 | Adult FMX | 0 | No | No | Red | AFMX-3 |
| B-3 | B | 3 | PEDO FMX | 0 | No | No | Purple | PFMX-3 |
| C-3 | C | 3 | 4 Horiz. BWX | 0 | No | No | Green | HBWX-3 |
| D-3 | D | 3 | 4 Vert. BWX | 90° CW | No | No | Blue | VBWX-3 |
| E-3 | E | 3 | PEDO BWX + PAX | 0 | No | No | Yellow | PBWPA-3 |
| F-3 | F | 3 | 7 Vert. BWX | 90° CW | No | No | Orange | 7BWX-3 |
| A-4 | A | 4 | Adult FMX | 0 | No | No | Red | AFMX-4 |
| B-4 | B | 4 | PEDO FMX | 0 | No | No | Purple | PFMX-4 |
| C-4 | C | 4 | 4 Horiz. BWX | 0 | No | No | Green | HBWX-4 |
| D-4 | D | 4 | 4 Vert. BWX | 90° CW | No | No | Blue | VBWX-4 |
| E-4 | E | 4 | PEDO BWX + PAX | 0 | No | No | Yellow | PBWPA-4 |
| F-4 | F | 4 | 7 Vert. BWX | 90° CW | No | No | Orange | 7BWX-4 |
| A-5 | A | 5 | Adult FMX | 0 | No | No | Red | AFMX-5 |
| B-5 | B | 5 | PEDO FMX | 0 | No | No | Purple | PFMX-5 |
| F-5 | F | 5 | 7 Vert. BWX | 90° CW | No | No | Orange | 7BWX-5 |
| A-6 | A | 6 | Adult FMX | 0 | No | No | Red | AFMX-6 |
| B-6 | B | 6 | PEDO FMX | 0 | No | No | Purple | PFMX-6 |
| F-6 | F | 6 | 7 Vert. BWX | 90° CW | No | No | Orange | 7BWX-6 |

FIG. 2

Subordinate PSPs (continued)

| Plate ID | Template = | Position = | Set Desc. | Rotation | Flip | Mirror | Color | Visual ID |
|---|---|---|---|---|---|---|---|---|
| A-7 | A | 7 | Adult FMX | 0 | No | No | Red | AFMX-7 |
| B-7 | B | 7 | PEDO FMX | 0 | No | No | Purple | PFMX-7 |
| F-7 | F | 7 | 7 Vert. BWX | 90° CW | No | No | Orange | 7BWX-7 |
| A-8 | A | 8 | Adult FMX | 0 | No | No | Red | AFMX-8 |
| B-8 | B | 8 | PEDO FMX | 0 | No | No | Purple | PFMX-8 |
| A-9 | A | 9 | Adult FMX | 90° CW | No | No | Red | AFMX-9 |
| A-10 | A | 10 | Adult FMX | 90° CW | No | No | Red | AFMX-10 |
| A-11 | A | 11 | Adult FMX | 90° CW | No | No | Red | AFMX-11 |
| A-12 | A | 12 | Adult FMX | 90° CW | No | No | Red | AFMX-12 |
| A-13 | A | 13 | Adult FMX | 90° CW | No | No | Red | AFMX-13 |
| A-14 | A | 14 | Adult FMX | 90° CW | No | No | Red | AFMX-14 |
| A-15 | A | 15 | Adult FMX | 90° CW | No | No | Red | AFMX-15 |
| A-16 | A | 16 | Adult FMX | 90° CW | No | No | Red | AFMX-16 |
| A-17 | A | 17 | Adult FMX | 90° CW | No | No | Red | AFMX-17 |
| A-18 | A | 18 | Adult FMX | 90° CW | No | No | Red | AFMX-18 |
| A-19 | A | 19 | Adult FMX | 90° CW | No | No | Red | AFMX-19 |
| A-20 | A | 20 | Adult FMX | 90° CW | No | No | Red | AFMX-20 |

DIGITAL RADIOGRAPHY PLATE IDENTIFICATION SYSTEM

CROSS-REFERENCE TO A RELATED APPLICATION

This application claims the benefit of U.S. provisional application Ser. No. 61/363,538, filed Jul. 12, 2010, which is incorporated herein by reference in its entirety.

BACKGROUND OF INVENTION

In the field of dentistry, various types of intra-oral sensors exist that are used for capturing images of the inside of teeth and surrounding anatomy (e.g., bone structure) by for example, exposing the anatomy and sensors to X-ray radiation. Such imaging techniques are well known, using such intra-oral sensors as, for example, X-ray sensitive film, X-ray sensitive phosphor plates, or X-ray sensitive digital imaging sensors such as a corded charge-coupled device (CCD) sensor.

When taking intra-oral images of patients, images are often captured on media such as radiographic film or photostimulable phosphor plates (also known as Phosphor Storage Plates or PSPs), which are then placed into a scanning apparatus to digitally extract the images from the media. The digitized images are then often transmitted to a receiving computer system where the images can be viewed either individually or along with other associated oral images within a specific viewing template. In the case where a multiple image set is being processed, the radiologist or dental technician must carefully and manually track the PSPs being used for the various images being acquired and, after placing the plates in the scanning apparatus, manually select an image template (initially), manually place each scanned image into the correct location within the selected template, and then manually direct the system to orient the image in one fashion or another so that it will be viewed from the proper perspective.

This process can include as many as twenty (20) images within a single template, often involves a significant amount of time, and can be prone to user error at one point or another in the process since all PSPs look (and are identified) exactly alike to both the human and the machine(s) involved in the process. Technical review of associated images is often necessary to identify the area of the oral cavity that is represented by the image(s) in order to identify the intended template and the proper location within the template that the image(s) is/are to be placed for display/viewing. Because of these limitations with current technology, the manual tracking, identifying, organizing and orienting of dental images for storage and display require a large amount of time for the radiologist/technician and/or dentist, resulting in lost productivity and delay in servicing patient needs.

To address some of the issues noted above, a computer program is available that requires a great deal of initial time and effort by the user to establish templates for sets of oral images (e.g. creating a mount in which the user must assign a number for each tooth image to be associated with the mount). In addition, the computer program requires the user to first establish a specific sequence of images and their rotations before image upload. Only after pre-established mount assignments, loading sequences, and rotational information has been provided by the user can the computer program provide some form of automated image processing. Because processing of images is based on specific pre-established mount assignments and loading sequences, user error in loading images (such as loading an image at the wrong time or out of sequence) will cause mis-assignment and mal-rotation of the image by the computer program.

To address this and other problems associated with PSPs described above, what is needed is a system for processing PSPs that does not require user-established assignments for templates or image loading sequences/rotations. Current technology does not provide PSPs or PSP imaging systems that incorporate unique identifiers such as marks, alphanumeric codes, bar codes, graphics, radio frequency identifiers, or coloring to (a) indicate to the dental technician/practitioner the proper plate set and plate to be used to obtain a specific image or set of images of desired oral locations and/or (b) to enable the computing system (either integral with or operatively connected to an imaging system) to automatically and properly identify, place, and orient intra-oral images obtained from PSPs within their intended "image set" or template without additional human intervention.

BRIEF SUMMARY

The subject invention provides innovative PSP identification methods and systems. In particular embodiments, the invention provides a PSP intra-oral image identification/coding system that provides for human identification of the correct PSPs to be used for specific intra-locations as well as computer system or image management component recognizable identifiers enabling images to be (a) automatically associated with an "image set" (or template), (b) placed in the proper location within the template and (c) properly rotated, flipped, etc. for proper orientation (as required).

A system of the invention can comprise: (a) a set or sets of scannable image media each coded with (i) unique, visual, and humanly recognizable radiolucent markings and (ii) unique processing system recognizable identifiers; and (b) a processing system able to associate the identifiers with extracted images from the scannable image medium and to process the extracted images based on the identifiers to facilitate automatic association with an image set, (and/or template) automatic identification of the image location, and automatic orientation (via rotation and/or flipping) of the image if needed. A graphical user interface can be included with the system(s) of the invention to automatically display processed digital images correctly and still enable user-interaction and/or image adjustments as these types of systems often do now.

The algorithms and methods utilized to instruct users and the associated processing system in the present invention are particularly advantageous in that they not only enable the subject digital radiographic plate identification system to provide time savings when obtaining intraoral images but also enable automatic and real-time classification and orientation of the digitized intra-oral radiography images.

In particular, the subject invention does not require the user to establish templates or loading sequences or image orientations prior to use which is an inefficient use of resources and is subject to user error when uploading images outside pre-established parameters. Accordingly, another advantage of the invention is that the order of obtaining and scanning identified images/plates has no effect on the outcome of the final template and associated images. Furthermore, the algorithms and methods described herein are designed to accommodate any practitioner's standards and conventions where imaging perspectives are concerned. For example, one dental practice may utilize a "standard" orientation set of templates and/or multi-image views while another may subscribe to what is known in the industry as the "military" orientation—both (and any other) can be dynamically configured within the methods described for an image processing system associated with this technology without altering the programming of the system.

One method of implementing the invention can include placing recognizable identifiers on scannable image media and entering the media's corresponding identifier-related information (e.g., media ID, template ID, position ID, and orientation index) into a table within an associated image processing/management (computer) system's database, wherein the processing system, upon receiving such an image from an internal or external media scanning apparatus, discerns the image's ID and, along with the system's database information automatically (a) identifies the proper image set (and causes the associated template to be displayed if not already done so), (b) identifies the image location within the set (and causes the image to be moved to that location in the template), and (c) identifies any orientation maneuvers the image might require for user viewing on the scanning device or processing system monitor (and causes the orientation to occur). In certain embodiments, the recognizable identifiers are pre-established as opposed to established by the user. In alternate embodiments, the recognizable identifiers are established by the user.

According to one embodiment of the invention, oral x-ray images are acquired from a patient utilizing PSPs (or a set of PSPs) that are identified in one or more locations with specific radiolucent identifiers intended for humans and/or radiopaque identifiers within the image field of the PSPs intended for computing systems and the PSP is later placed into a scanning device. The scanning device reads, extracts, and transmits a digital version of the image (said image including the radiopaque computer readable identifier) from the PSP to a connected (wireless or wired) computing/processing system. When the processing system receives an image from such a media scanning apparatus, it discerns the image's ID from within the image itself (e.g., via Optical Character Recognition) and along with the system's PSP-ID-related database information, the processing system (a) identifies the proper image set and causes the associated template to be automatically displayed if not already displayed, (b) identifies the image location within the set and automatically causes the image to be moved to that location in the template, and (c) identifies any orientation maneuvers the image might require for user viewing on the scanning device or processing system monitor and automatically causes the orientation to occur. For example, if the identifier indicates (via the associated database information) the need for 90° clockwise rotation, the processing system will automatically and properly orient the image 90° in the clockwise direction before or after placing the image in the proper location within its associated template for user viewing.

In an alternate embodiment, the system comprises: scannable image media, each coded with human-readable and (radiolucent or radiopaque) machine-readable identifiers, a scanning apparatus having the ability to read, extract, digitize, and transmit both the digital image as well as the coded machine-readable identifiers, and a processing system able to associate respective coded machine readable identifiers with received digital images transmitted to the processing system and to process the images based on their identifiers to automatically select and associate with which image set (or template) the extracted images are to be grouped and/or displayed as well as identify and/or place the image in the correct location and to also orient the image properly.

In an alternate embodiment, the system comprises: scannable image media, each coded with human-readable and machine-readable identifiers, a scanning apparatus having the ability to read, extract, digitize, and transmit both the digital image as well as the coded machine-readable identifiers, and a processing system able to associates respective coded machine readable identifiers with extracted digital images transmitted to the processing system as a "data set" and to process the images based on the identifiers to automatically select and associate with which image set (or template) the extracted images are to be grouped and/or displayed as well as identify and/or place the image in the correct location and to also orient the image properly.

In certain embodiments, the processing system is provided within the scanning apparatus. In alternative embodiments, the processing system is separate from that of the scanning apparatus (e.g., the processing system is provided in a computer system separate from the scanning apparatus).

In a method of use where the processing system is located within or integral with the scanning apparatus, one embodiment utilizes encoded scannable image media provided with human and/or machine-readable identifiers and the scanning apparatus reads a predetermined series of scannable image media, extracts the images and reads their associated identifiers, combines the individual images with their identifiers, and creates a combined/concurrent data stream or file containing these image/identifier pairs and transmits the entire, separately identified image set to a processing/viewing system. The processing/viewing system utilizes the identification transmitted with the image set (and/or internally with each image within the set) in conjunction with an identification table within the processing/viewing system to automatically save and/or display the image set and associate each acquired image within the transferred file with the appropriate image set, image location, and orientation for user viewing on the processing system.

Where the processing system is operably connected to a scanning apparatus, an image is acquired from a patient onto PSP that is coded with human and/or machine-readable identifiers and is placed into a scanning device. The scanning device extracts and transmits a digital version of the image on the PSP along with the coded identifier to a computer system capable of processing said images containing coded identifiers. The image processing system within thin the computer system associates the coded identifier with the digital image and further processes the image. Based on the coded identifier associated with the image, the processing system identifies with which image set the image is to be grouped as well as the image location within the image set. In addition, the processing system utilizes the coded identifier associated with the image to ascertain whether the image needs to be modified for proper orientation. For example, if an image's coded identifier indicates to the image processing system the need for 90° clockwise rotation, the image processing system will automatically rotate the image 90° in the clockwise direction for correct orientation and user viewing.

According to the subject invention, the association of the coded identifiers with images are pre-established as opposed to being established by a user. Alternatively, the association of which image is associated with which coded identifier can be established by the user.

In certain embodiments, the coding system for the scannable image media is based on colors, numbers, alphabet letters, graphic images, barcodes, magnetic strip, or any other symbols or combination of these identifiers that are easily identified by a user and/or machine. In a preferred embodiment, the scannable image media are phosphorous plates, wherein the Master plate for a set of phosphorous plate images is coded with an easily identifiable visual indicator, such as a color.

In other embodiments, radiolucent, sterile plastic film sleeves (also referred to herein as "sleeves" or "envelopes") are provided that are a part of the coding/identification system. For example, the subject invention provides PSP sterile sleeves that include color and/or radiolucent graphical codings that indicate targeted oral locations to further assist in the practitioner's identification of the proper PSP to be used to acquire an oral image without affecting the quality of the image obtained from the PSP.

DETAILED DISCLOSURE

The subject invention provides novel methods, products, and/or systems for intra-oral image PSP identification/coding/processing. The method/system provides identifiers for human assistance in plate set and individual plate selection that does not exist today, as well as machine-readable identifiers enabling an included or attached image management process or system to perform automatic "image set" identification and display of the proper/associated image viewing template, automatic image placement within the displayed template, and automatic image orientation within the specified location if required.

In certain related embodiments, specific PSPs and/or their associated radiolucent sterile sleeves are coded with a recognizable identifier. In one embodiment, radiolucent sterile sleeves are color coded to assist the user in identifying the correct PSP set and/or PSPs to be used for specific image sets.

In other related embodiments of the technology, radiolucent identifying characters for, and/or graphical representations indicating, targeted oral locations are placed on the PSPs and/or corresponding sterile "sleeves" to further assist the user in identifying the correct PSP set and/or PSPs to be used for specific images within one or more image sets.

In certain embodiments, the recognizable identifiers are pre-established as opposed to established by the user. In alternate embodiments, the recognizable identifiers are established by the user.

In a specific example, a set of PSPs are provided, each of which contain a coded identifier (such as one or more alphanumeric characters and/or a bar-code) that is associated with (a) an image set; (b) an image location within the specific set; and/or (c) a specific orientation for that image when used within this set. Each set of PSPs represents specific dental x-ray common image sets (i.e. full mouth sets, horizontal bitewing sets, vertical bitewing sets, etc.). In practical use, a dental technician/practitioner would select an appropriate plate set based on the set of images desired, and then select a PSP from that set based on the specific image to be obtained. Once the appropriate oral image is obtained from the patient, the PSP is placed into a radiographic plate reader device/system. The radiographic plate reader device/system includes or is connected to a processing, system that is able to electronically and automatically: (1) associate the PSP's coded image with the proper template; (2) following identification of the proper template in step (1), place the PSP image in the correct location within the proper template; and (3) determine whether the image is in a proper orientation and, if necessary, rotate the image into the proper orientation.

Once properly identified and oriented, the images and/or image set are/is then automatically uploaded into an existing, connected computer system for viewing and associating with a specific patient. The subject invention also allows for the use of solo or wild-card PSPs for individual image capture and transfer without being affiliated with a specific template or set of images such that the practitioner can manually place and orient an image as desired.

In related embodiments, a "master" image plate within each plate set will not only contain a coded identifier that specifies the image set, location, and orientation, but is also coded with a same standard recognizable identifier (such as by color and/or radiolucent image) to visually indicate with which image set all of the images are to be grouped, further ensuring that the template will be identified before any other plate images are processed and/or transferred.

One advantage of the subject system and methodology is its ability to be integrated into existing/standard phosphorous plate readers (e.g., Scan X or DenOptix) that, without modification, can capture both the plate's image and the plate's specific identification (ID) code/markings and transfer the captured ID information and images to existing Dental Practice Management Systems and/or imaging and patient-data storage systems (e.g., Dentrix). Another useful feature of the subject technology is that it requires little or no modification to such existing image readers or transfer device/software. Further, the subject technology enables automatic and correct template selection, image locating, and orientation of uploaded digital radiographic images, eliminating much of the human intervention and time currently required by existing systems.

In an exemplary embodiment, an intra-oral image is captured using a radiation source (e.g., an X-ray tube) and a scannable image medium (e.g., a photostimulable phosphor storage plate or PSP). The X-ray tube emits a dose of X-ray radiation toward the oral structure of interest. Some of the X-ray radiation passes through the oral structure and exposes the scannable image medium, capturing an image of the oral structure on the image medium. In accordance with various embodiments, the scannable image medium may include a radiographic film, a photosensitive film, or a photostimulable phosphorous plate, all of which are well known in the art. Other scannable media may be possible as well Preferably, the scannable medium is a PSP.

According to the subject invention, the scannable image medium includes one or more coded identifiers that provide information regarding the image that is captured on the scannable image medium. In a preferred embodiment, the coded identifiers provide information regarding the image set, image location, and/or proper rotation of the image captured on the scannable image medium. According to the subject invention, the coded identifier can be machine-readable, visual, and/or tactile. According to the subject invention, the coded identifier can be a color, number, alphabet letter, bar-code, electronic signal, magnetic strip, or any other identifiers that are easily read by a human user and/or machine.

According to the subject invention, the association of the coded identifiers with images are pre-established as opposed to being established by a user. Alternatively, the association of which image with which coded identifier can be established by the user.

Figure 1:
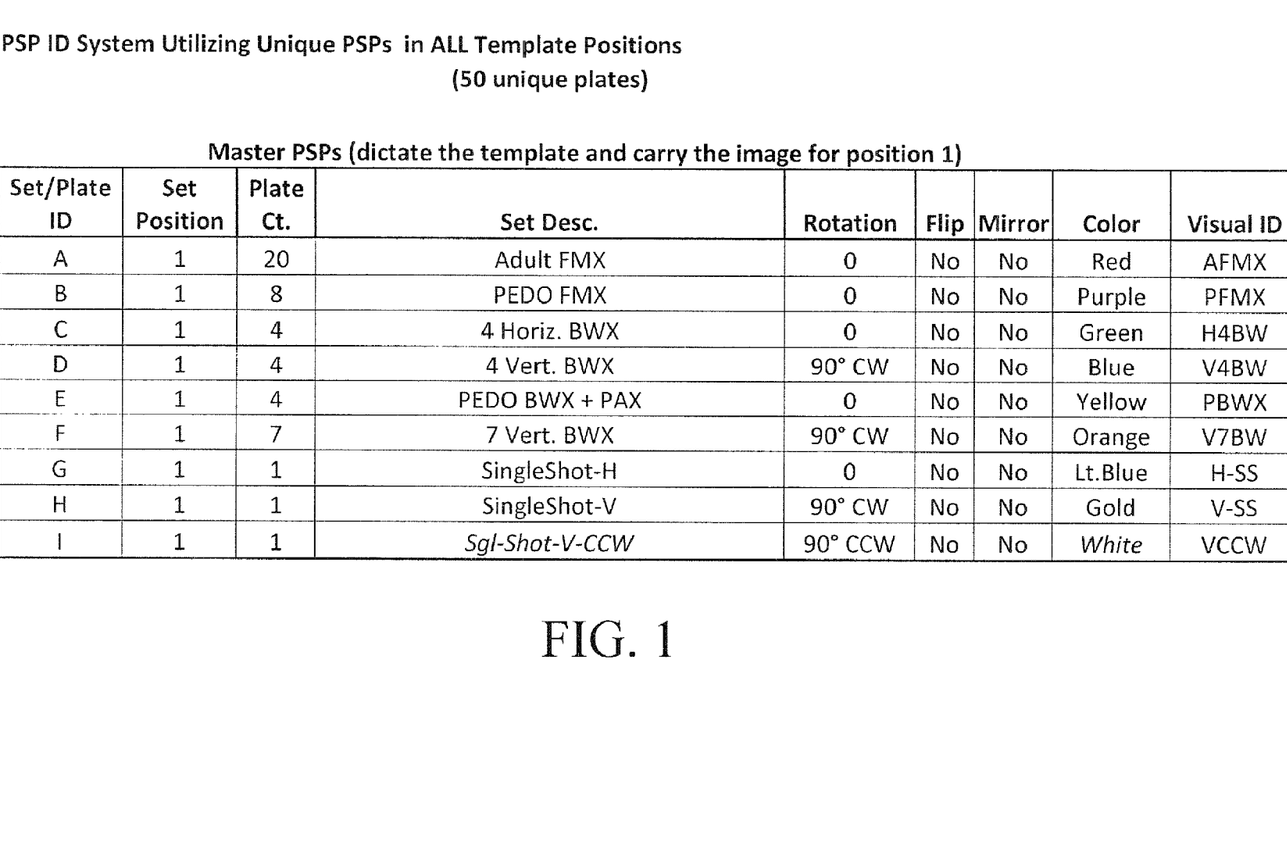
FIG. 1 is an illustration of an example "master and subordinate" coding system that can be used to identify several sets of PSPs and the images contained within these sets for use in accordance with one or more embodiments of the invention.

As illustrated in FIG. 1, a representative selection of colors and alpha-numeric coded identifiers can be used to identify the images depicted on each PSP for a set of dental images to be acquired from a patient using a "Master" and "Subordinate" PSP method. In this embodiment, the "Master" coding system dictates the appropriate identification and display of the proper image viewing template for a set of PSPs and the "Subordinate" coding system specifies the appropriate image placement within the image viewing template as well as the appropriate image orientation within the specified location within the template. This identification method reduces the number of uniquely identified PSPs by re-using "subordinate" PSPs in various sets dictated by the accompanying "master" PSP.

Figure 3:
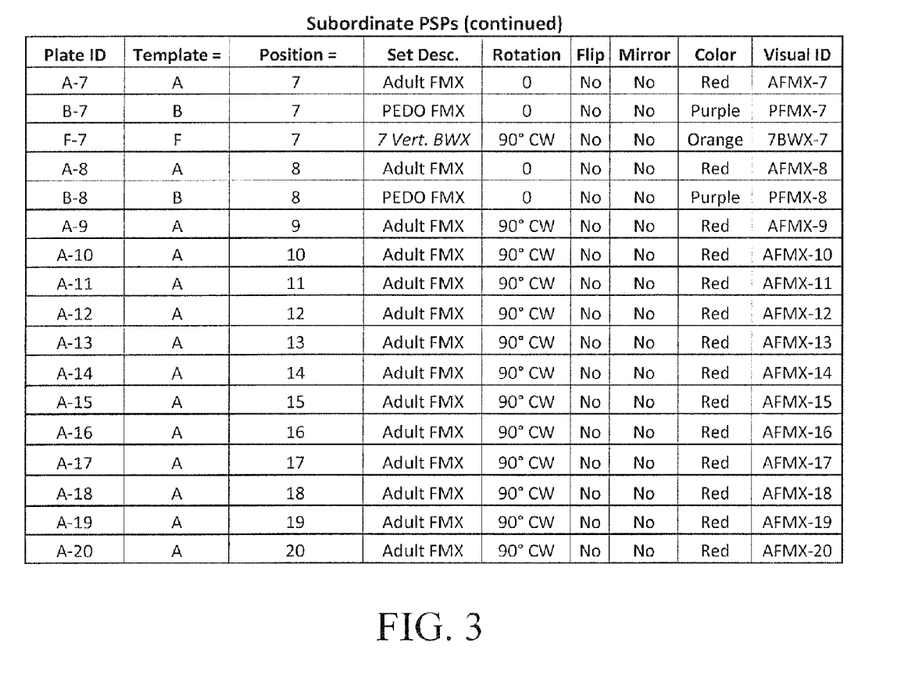
FIG. 3 is an example Full Mouth X-Ray Image Template identifying an image set, providing image locations within the image set, and visual orientation of various images within the set.

For example, as illustrated in FIG. 1, a Master PSP for a full set of adult mouth images ("Adult FMX"—see FIG. 3) is identified using the color Red and having a coded number 1. Data regarding the image position and image rotation position of an associated Subordinate PSP is provided by an alphabet letter. For example, a PSP coded with a letter "A" and associated with a Red plate coded with a number 1 would be read by a computing system to mean position 2 in the set of Adult FMX images illustrated in FIG. 3 and that no rotation would be necessary for the image in this particular template. A PSP with the letter "H" following and/or associated with a Red plate having a coded number 1 would be read by a computing system to mean position 9 in the set of Adult FMX images and that a 90° rotation in image position would be necessary for proper image viewing within the Adult FMX image set. Additional orientation maneuvers such as "flip" and "mirror" can also be assigned to each individual image within a template. The abbreviation "CW" and "CCW" represent "clockwise" and "counterclockwise," respectively. The terms "flip" and "mirror" represent rotations of the image about a central axis that bisects the image, where the image can be folded in half over the axis. The symbol "0" represents no rotation of the image.

Figure 2:
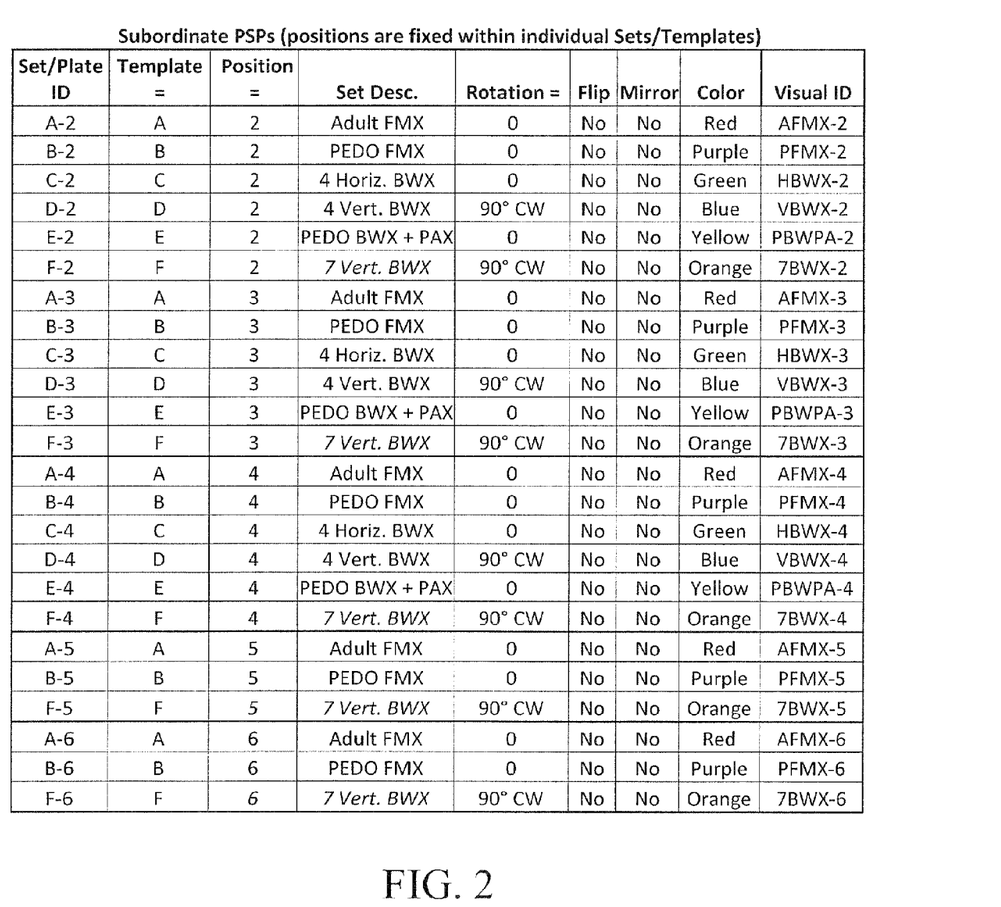
FIG. 2 is an illustration of another example coding system where each plate has a specific location and orientation within a single/individual Oral Image Template for use in accordance with one or more embodiments of the invention.

As illustrated in FIG. 2, a representative selection of colors and alpha-numeric coded identifiers can be used on each PSP to identify that PSP's specific template, position, and orientation without utilizing a master/subordinate method. For example, a PSP identified as "D-4" will always be placed in the Four Vertical Bitewing template in position four with a 90 degree rotation. The abbreviation "CW" and "CCW" represent "clockwise" and "counterclockwise," respectively. The terms "flip" and "mirror" represent rotations of the image about a central axis that bisects the image, where the image can be folded in half over the axis. The symbol "0" represents no rotation of the image.

In one embodiment, a scanning apparatus is provided that is capable of scanning the image media to digitally extract a captured image from the image media. Furthermore, in accordance with a related embodiment, each scannable image medium is encoded with a machine-readable coded identifier and the scanning apparatus is capable of reading the coded identifier of any scannable image medium. The encoded identifier is associated with a particular image set, image position, and/or image rotation position. A first plurality of scannable image media may have a same standard encoded identifier to specify a set of images to be grouped together. A second encoded identifier on each of the scannable image media in the first plurality of scannable image media may be used to identify the particular image within the image set as well as the proper rotation of the image. The versatility of the subject invention allows combinations of templates, template positions, and orientations/rotations that can be programmed to fit a practitioner's method and perspective of obtaining oral images.

According to one embodiment of the invention, the scanning device comprises a laser scanner along with the media ID reader. In certain embodiments, the scanning device further includes a digital processing and network transmitting apparatus which is operationally connected to the laser scanner and the media ID reader. The laser scanner is capable of scanning an image from a scannable image medium (e.g., a radiographic film or a PSP) to extract a digital image. The laser scanner may be configured to scan a photostimulable phosphor plate or a radiographic film in accordance with various embodiments. Also, the standard coded media ID reader is capable of reading an encoded identifier on a scannable image medium. The standard identifier reader may be configured as an optical reader, a magnetic reader, or a bar code reader in accordance with various embodiments. Other types of readers may be possible as well, in accordance with various embodiments. A user places a scannable image medium into the scanning apparatus to have both the exposed image and the standard coded identifier read by the laser scanner and the standard coded identifier reader, respectively. The scanning apparatus is operationally connected to a computing system via a network (wired or wireless).

The processing system includes any digital instrumentation capable of processing digitized image data and/or encoded identifiers read by the scanning apparatus of the invention. Such digital instrumentation, as understood by the skilled artisan, can process communicated image and/or identification data by applying algorithm operations of the subject invention. Preferably, the digital instrumentation is a microprocessor digital signal processor (DSP), personal desktop computer, a laptop, and/or a portable palm device.

The digitized image(s) and encoded identifiers from the scanning apparatus are transmitted to a processing system for image processing. In one embodiment, the processing system is located within the scanning apparatus. In alternate embodiments, the processing system is located within a computer system that is separate from but connected to the scanning apparatus.

In addition to processing the digitized data images, the computer system can also be responsible for maintenance of acquired digital image data as well as the maintenance of the radiographic image identification system itself. The computer system can also detect and act upon user input via user interface means known to the skilled artisan (i.e., keyboard, interactive graphical monitors, mouse, etc.). In one embodiment, the computer system further comprises means for storing and means for outputting processed data. The computer system can be general purpose or application specific.

The algorithms/logic utilized to instruct the computing system in the present invention are particularly advantageous in that they enable the subject digital radiography plate identification system to provide real-time results as well as automatic and real-time classification and orientation of digitized intra-oral radiography images. Such algorithms/logic (also referred to herein as instructions or software) can be provided as a computer program product, tangibly embodied in an information carrier (e.g., in a machine-readable storage device or in a propagated signal, for execution by a programmable processing system). Such instructions can be written in any form of programming language, including compiled or interpreted languages, and they can be deployed in any form, including as a stand-alone program or as a module, component, subroutine, or other unit suitable for use in a computing system. The machine-readable storage devices include, by way of example, diskettes, CD-ROM disks, DVD-ROM disks, zip drives, portable storage devices, non-volatile memory, semiconductor memory devices (e.g., EPROM, EEPROM), flash memory devices, magnetic disks such as internal hard disks and removable disks, magneto-optical disks, or any other computer-readable storage medium, wherein the computer program code is loaded into and executed by the computing system. Optionally, the operational algorithms of the subject invention can be programmed directly onto the CPU using any appropriate programming language and/or human user interface device or method.

Figure 4A:
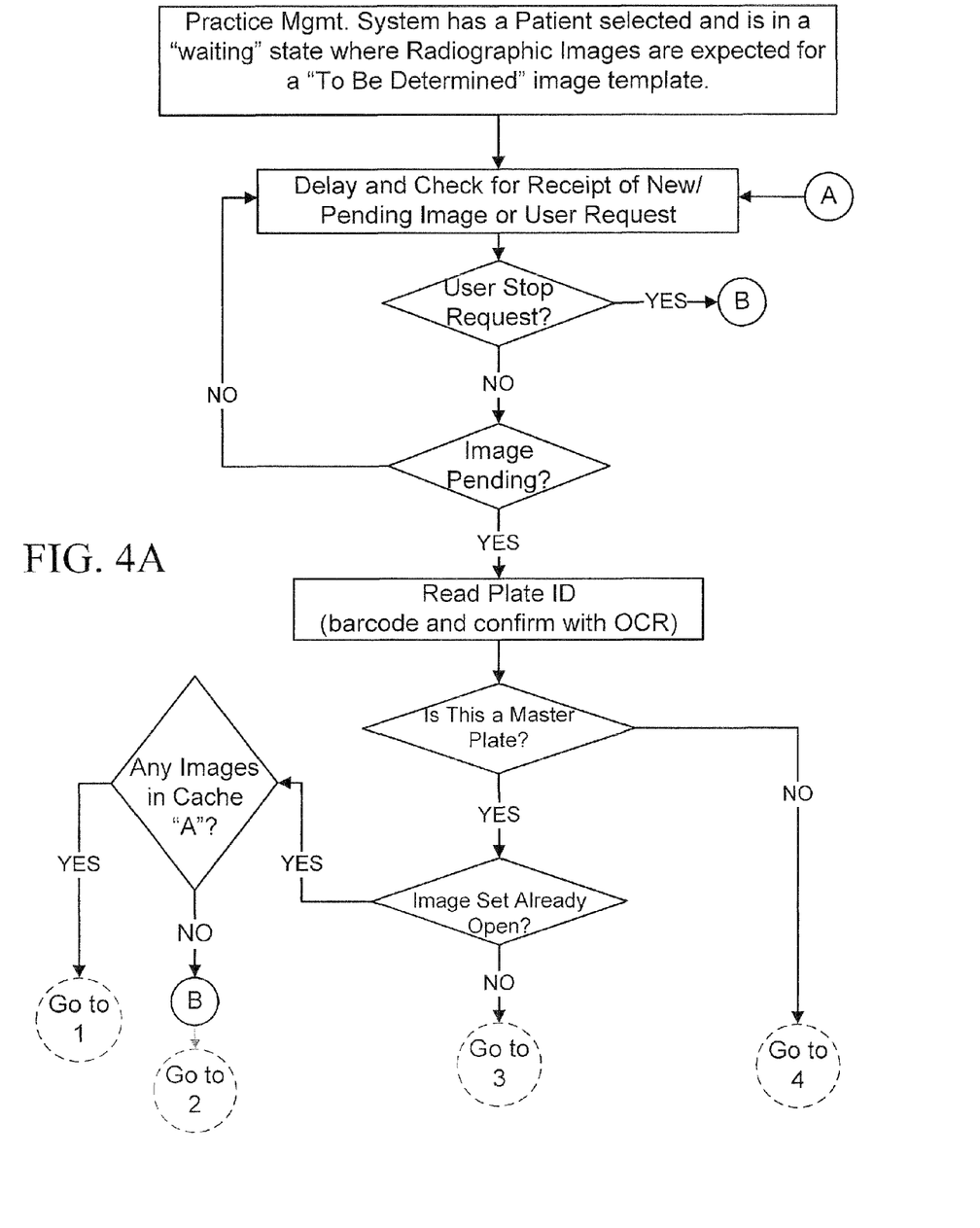
FIG. 4 is a schematic flow diagram of a method for automatically identifying an image set, providing an image location within the image set, and orienting the image in accordance with the subject invention.
Figure 4B:
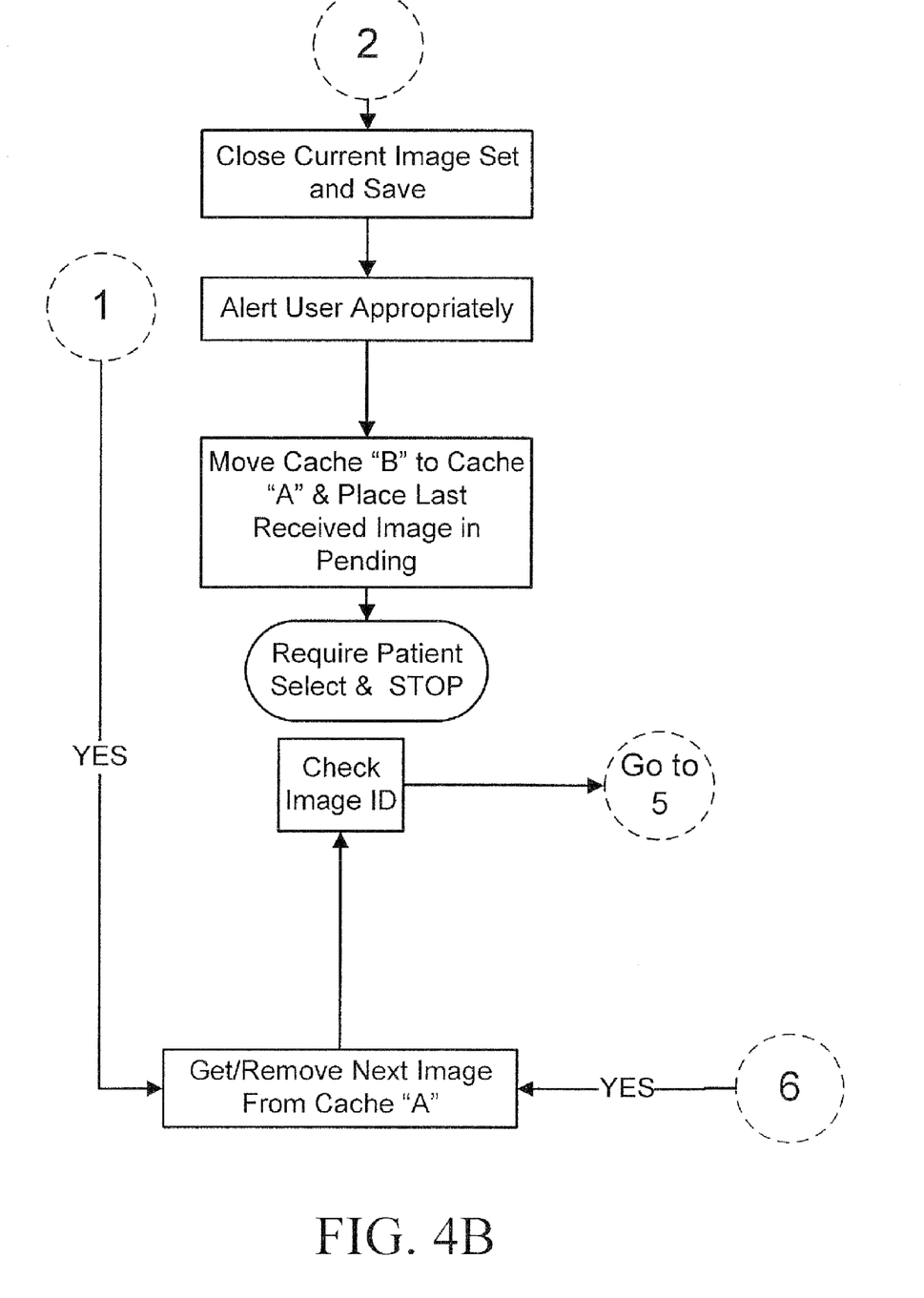
Figure 4C:
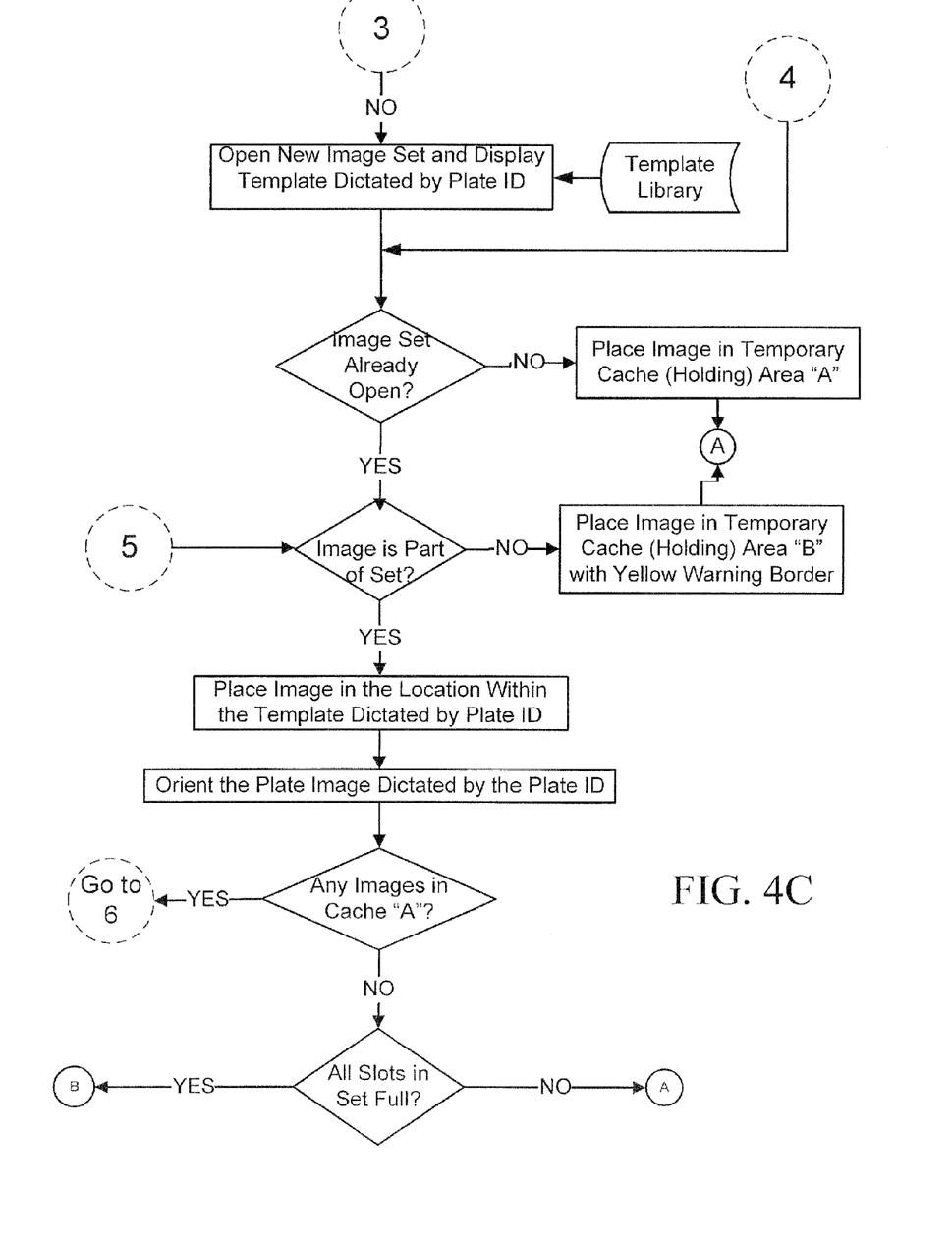

In one embodiment, as illustrated in FIG. 4, a program product is provided that includes instructions to perform operations that support automatic identification of an image set, provision of an image location within the image set, and orientation of the image that includes image (radiographic and/or digitized) entry. Prior to processing an image, a patient identifier has been selected and is awaiting images for an image set. When establishing an image set of images, the first step generally includes assessing whether a new or pending image is present or if a user request to stop the process has been entered. Should a user stop request be entered, the current image set is closed and saved. The last received image is placed in a cache for pending images and all other images that have already been processed are placed into a temporary cache (holding area) for an already established image set associated with the patient identifier. The user is then alerted regarding the closing and saving of the image set and requested to associate the image set with the patient identifier by selecting a patient identifier.

Should a new or pending image be present, the associated identifier from the phosphorous plate is read and confirmed. Should the identifier indicate the image is a "Master Plate," the program product will assess if an image set has already been established with processed images already associated with the Master Plate (image set).

If an image set has already been established, any images that have been placed in a temporary cache (holding area) "A" are retrieved and assessed to verify whether they are a part of the image set. Should an image not be a part of the image set, it is placed in a temporary cache (holding area) "B" with an alert or warning indicating the image is not associated with an image set. Should an image be confirmed as being a part of the image set, the image is placed within a location template dictated by the identifier and the image is properly oriented in accordance with the identifier. This process is repeated until all of the images for an images set have been entered. Once an image set is completed (all images have been entered into slots for an image set), the program product closes the current image set and saves it The user is alerted of this action and any pending images that could not be confirmed to be part of the image set (such as those placed in cache "B") are placed in cache "A" to await further processing.

If an image set has not been established for the Master Plate, an image set and display template dictated by the identification code/marking is established. The display template is selected from a template library that is preferably stored in a database.

Should the identification code/marking indicate the image is not a "Master Plate," the program product will assess if an image set has already been established with processed images already associated with the image set. Should an image set have been established, the image will be placed in cache "A" to await processing of the associated "Master Plate." Following processing of the "Master Plate," each image in cache "A" is placed within a location template dictated by the identification code/marking and the image is properly oriented in accordance with identification code/marking. This process is repeated until all of the images for an image set have been entered. Once an image set is completed (all images have been entered into slots for an image set), the program product closes the current image set and saves it. The user is alerted of this action and any pending images that could not be confirmed to be part of the image set (such as those placed in cache "B") are placed in cache "A" to await further processing.

The systems and methods described herein can be implemented in digital electronic circuitry or in computer hardware, firmware, software, or in combinations thereof. Preferably, the computing system comprises a central processing unit (CPU) having sufficient processing power to perform algorithm operations in accordance with the subject invention.

In certain embodiments, the computer system comprises a memory capacity sufficiently large to perform algorithm operations in accordance with the subject invention. The memory capacity of the invention can support loading a computer program code via a computer-readable storage medium, wherein the program contains the source code to perform the operational algorithms of the subject invention. Optionally, the memory capacity can support directly programming the CPU to perform the operational algorithms of the subject invention. A standard bus configuration can transmit data between the CPU, memory, ports and any communication devices.

In addition, as understood by the skilled artisan, the memory capacity of the computing system can be expanded with additional hardware and with saving data directly onto external media including, for example, without limitation, diskettes, zip drives, non-volatile memory and CD-ROMs.

Communication devices such as wireless interfaces, cable modems, satellite links, microwave relays, cable relays, fiber optic relays, and traditional telephonic modems can transfer digital image data from a scanning apparatus to a computing system via a network. Networks available for transmission of clinical data include, but are not limited to, local area networks, intranets and the open internet. A browser interface can be incorporated into communications software to view the transmitted data.

Advantageously, a browser or network interface is incorporated into the computing system to allow the user to view the processed image data in a graphical user interface device, for example, a monitor. The results of algorithm operations of the subject invention can be displayed in the form of the interactive graphics.

It should be understood that the examples and embodiments described herein are for illustrative purposes only and that various modifications or changes in light thereof will be suggested to persons skilled in the art and are to be included within the spirit and purview of this application.

We claim:

1. A method for automatically processing and orienting dental radiographic images comprising the steps of:
    a) encoding each of a set of scannable image media with identifiers regarding image location and orientation;
    b) reading the scannable image media with a scanning apparatus to produce a set of digital data images and transmitting the set of digital data images to a processing system; and
    c) processing the set of digital data images and their identifiers within the processing system: to determine an image location for each digital data image within the first set of digital data images; to ascertain whether any digital data image in the set of digital data images needs to be properly oriented; and to automatically and properly orient any digital data image in the set of digital images ascertained to need proper orientation.

2. The method of claim 1, wherein the scannable image media further comprises a same standard identifier that groups together each scannable image medium in the set of scannable image media; and processing the set of digital data images with the same standard identifier to associate the set of digital data images with the set of scannable image media.

3. The method of claim 1, wherein the identifier is a visual and/or machine-recognizable identification.

4. The method of claim 3, wherein the identifier selected from the group consisting of: colors, numbers, alphabet letters, symbols, barcodes, electronic signals, and magnetic strips.

5. The method of claim 1 wherein the scannable image media is selected from the group consisting of: photostimulable phosphor plate, radiographic film, and photosensitive film.

6. The method of claim 1, wherein the processing system is located within the scanning apparatus.

7. The method of claim 6, further comprising the step of transmitting the processed set of digital data images to a computer system.

8. The method of claim 7, wherein the computer system can further perform any one or more of the following steps: store the processed set of digital data images; output the processed set of digital data images; maintain the processed set of digital data images; and detect and act upon user commands to manipulate the set or sets of digital data images.

9. The method of claim 1, wherein the processing system is separate from the scanning apparatus and is located within a computer system.

10. The method of claim 9, wherein the computer system can further perform any one or more of the following steps: store the processed set of digital data images; output the processed set of digital data images; maintain the processed set of digital data images; and detect and act upon user commands to manipulate the set of digital data images.

11. The method of claim 1, further comprising the step of providing encoding film holders for each scannable image medium of the set of scannable image media, wherein each film holder includes a visual identifier.

12. The method of claim 11, wherein the visual identifier is selected from the group consisting of colors, numbers, alphabet letters, symbols, and graphical representations of oral locations.

13. A system to automatically process and orient dental radiographic images, said system comprising:
 a) a set of scannable image media encoded with identifiers regarding image location and orientation;
 b) a scanning apparatus with the ability to read the scannable image media, produce a set of digital data images, and transmit the set of digital data images to a processing system; and
 c) a processing system with the ability to determine an image location for each digital data image within the first set of digital data images; to ascertain whether any digital data image in the set of digital data images needs to be properly oriented; and to automatically and properly orient any digital data image in the set of digital images ascertained to need proper orientation.

14. The system of claim 13, wherein the set of scannable image media is also encoded with a same standard identifier to group together each scannable image medium in the set of scannable image media; and wherein the processing system further comprises the ability to associate the set of digital data images with the set of scannable image media based upon the same standard identifier.

15. The system of claim 13, wherein the identifier is a visual and/or machine-recognizable.

16. The system of claim 15, wherein the identifier is selected from the group consisting of: colors, numbers, alphabet letters, symbols, barcodes, electronic signals and magnetic strips.

17. The system of claim 13, wherein the scannable image media pis selected from the group consisting of photostimulable phosphor plate, radiographic film, and photosensitive film.

18. The system f claim 13, wherein the processing system is located within the scanning apparatus.

19. The system of claim 13, wherein the processing system is located with a computer system.

20. The system of claim 13, further comprising film holders for each scannable image medium of the set of scannable image media, wherein each film holder includes a visual identifier.

21. The system of claim 20, wherein the visual identifier is selected from the group consisting of colors, numbers, alphabet letters, symbols, and graphical representations of oral locations.

22. The system of claim 13, further comprising a graphical user interface.

23. A computer program product, tangibly embodied in an information carrier, for automatically processing and orienting dental radiographic images in a processing system, the product comprising instructions to cause the processing system to: associate a set of digital data images with a set of scannable image media; determine an image location for each digital data image within the first set of digital data images; ascertain whether any digital data image in the set of digital data images needs to be properly oriented; and automatically and properly orient any digital data image in the set of digital images ascertained to need proper orientation.

24. The method of claim 1, wherein a template is provided for the set of image locations and wherein, based on the identifiers, the processing system first determines with which template each digital image is to be associated.

25. The method of claim 1, wherein the digital data images are intra-oral images.

26. The method of claim 5, wherein the scannable image media is a photostimul able phosphor plate and the scanning apparatus is a photostimulable phosphor plate reader.

27. The system of claim 13, wherein the scannable image media is a photostimulable phosphor plate and the scanning apparatus is a photostimulable phosphor plate reader.

28. The system of claim 13, wherein the scanning apparatus comprises an identifier reader.

29. The system of claim 28, wherein the identifier reader is selected from the group consisting of an optical reader, a magnetic reader, and a bar code reader.

30. The system of claim 19, further comprising a means for transferring digital image data from the scanning apparatus to the computer system.

31. The system of claim 30, wherein the transferring means is selected from the group consisting of: wireless interfaces, cable modems, satellite links, microwave relays, cable relays, fiber optic relays, and traditional telephonic modems.

* * * * *

UNITED STATES PATENT AND TRADEMARK OFFICE
CERTIFICATE OF CORRECTION

PATENT NO. : 8,374,461 B2
APPLICATION NO. : 13/180886
DATED : February 12, 2013
INVENTOR(S) : Geoffrey Humphreys et al.

Page 1 of 1

It is certified that error appears in the above-identified patent and that said Letters Patent is hereby corrected as shown below:

In the Specifications:

Column 1,
Lines 15-16, "by for example" should read --by, for example,--

Column 2,
Line 25, "intra-locations" should read --intra-oral locations--

Column 8,
Line 36, "(DSP), personal" should read --(DSP), a personal--

In the Claims:

Column 12,
In Claim 17, Line 13, "media pis selected" should read --media is selected--

Column 12,
In Claim 17, Lines 13-14, "consisting of photostimulable" should read
--consisting of: photostimulable--

Column 12,
In Claim 18, Line 16, "system f claim" should read --system of claim--

Column 12,
In Claim 26, Line 48, "photostim able" should read --photostimulable--

Signed and Sealed this
Fourteenth Day of May, 2013

Teresa Stanek Rea
*Acting Director of the United States Patent and Trademark Office*